US008501112B2

(12) United States Patent
Miyamura et al.

(10) Patent No.: US 8,501,112 B2
(45) Date of Patent: Aug. 6, 2013

(54) BODY FLUID ANALYSIS FIXTURE

(75) Inventors: Kazuhiro Miyamura, Kyoto (JP); Kazutaka Okamoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 13/216,096

(22) Filed: Aug. 23, 2011

(65) Prior Publication Data

US 2012/0045375 A1 Feb. 23, 2012

(30) Foreign Application Priority Data

Aug. 23, 2010 (JP) ................................ 2010-186253

(51) Int. Cl.
*G01N 33/48* (2006.01)

(52) U.S. Cl.
USPC ........... 422/417; 422/400; 422/430; 422/68.1

(58) Field of Classification Search
USPC ................................ 422/68.1, 400, 417, 430
See application file for complete search history.

(56) References Cited

U.S. PATENT DOCUMENTS

| | | | | |
|---|---|---|---|---|
| 3,706,305 | A * | 12/1972 | Berger et al. | 600/575 |
| 7,188,734 | B2 * | 3/2007 | Konrad | 210/516 |
| 2003/0221477 | A1 * | 12/2003 | Pierskalla et al. | 73/1.03 |
| 2011/0192218 | A1 * | 8/2011 | Miyamura et al. | 73/64.56 |
| 2011/0192219 | A1 * | 8/2011 | Miyamura | 73/64.56 |
| 2011/0194977 | A1 * | 8/2011 | Miyamura et al. | 422/68.1 |

FOREIGN PATENT DOCUMENTS

JP 2004-257768 A 9/2004

* cited by examiner

*Primary Examiner* — Lyle Alexander
(74) *Attorney, Agent, or Firm* — Alleman Hall McCoy Russell & Tuttle LLP

(57) ABSTRACT

The present invention is intended to, in a configuration in which a liquid container for analysis sealed by a sealing member is penetrated by a penetrating member, prevent the sealing member from being unexpectedly broken to leak a liquid for analysis. Also, the present invention has: a container holder part that holds a liquid container for analysis; a penetrating member that penetrates a sealing member of the liquid container for analysis; a first moving mechanism that enables the penetrating member to be moved between a hole making position and a receding position; and a second moving mechanism that enables the penetrating member moved to the hole making position by the first moving mechanism to be moved toward the sealing member to a penetrating position where the penetrating member penetrates the sealing member.

4 Claims, 12 Drawing Sheets

BODY FLUID ANALYSIS FIXTURE

TECHNICAL FIELD

The present invention relates to a body fluid analysis fixture that analyzes a body fluid such as blood, and more particularly, to a body fluid analysis fixture having a penetrating member that penetrates a sealing film of a liquid container for analysis.

BACKGROUND ART

As this sort of body fluid analysis fixture, as disclosed in Patent literature 1, there is a cartridge that is detachably attached to a micro blood cell counter main body. The cartridge is provided with: a measuring flow path that circulates a diluted sample blood; and a detecting part that is provided in the flow path and intended to measure the sample blood. Also, one end on an upstream side of the measuring flow path is provided with a capillary that quantitatively collects blood.

When the cartridge is used to measure the sample blood, the capillary is first stuck into a fingertip of a test subject to quantitatively collect blood into the capillary on the basis of a capillary phenomenon of the capillary. Subsequently, by sticking the capillary into a diluent liquid container that contains a diluent liquid, and then peeling a sealing film that seals an air hole provided through the diluent liquid container, the diluent liquid container is opened to the atmosphere to introduce the diluent liquid into the capillary.

The present inventor is now advancing the development of a cartridge having a mechanism that uses a penetrating member to penetrate the sealing film of the diluent liquid container.

For this purpose, a configuration in which the penetrating member is simply provided at a position facing the sealing film of the diluent liquid container to move the penetrating member back and forth with respect to the sealing film is considered; however, at the time of attaching the diluent liquid container, or subsequently moving the cartridge, the penetrating member may unexpectedly come into contact with the sealing film to penetrate it.

CITATION LIST

Patent Literature

Patent Literature 1: JP 2004-257768A

SUMMARY OF THE INVENTION

Technical Problem

Therefore, the present invention is made to solve the above problem at least in part, and has a main desired object to, in a configuration in which a liquid container for analysis sealed by a sealing member is penetrated by a penetrating member, prevent the sealing member from being unexpectedly broken by the penetrating member to leak a liquid for analysis.

Solution to Problem

That is, a body fluid analysis fixture according to the present invention has: a container holder part that holds a liquid container for analysis that is sealed by a sealing member; a penetrating member that penetrates a sealing member of the liquid container for analysis held by the container holder part; a first moving mechanism that enables the penetrating member to be moved between a hole making position that is an upper side in an out-of-plane direction of the sealing member and a receding position that is separated from the hole making position in a direction orthogonal to the out-of-plane direction of the sealing member; and a second moving mechanism that enables the penetrating member moved to the hole making position by the first moving mechanism to be moved toward the sealing member to a penetrating position where the penetrating member penetrates the sealing member.

If so, penetrating operation on a sealing film by the penetrating member can be performed so as to move from the receding position to the hole making position along the direction orthogonal to the out-of-plane direction of the sealing film and then move to the penetrating position. Based on this, because, before the penetrating operation, the penetrating member is at the receding position, the penetrating member can be prevented from unexpectedly coming into contact with the sealing film before the penetrating operation. Accordingly, the sealing film can be prevented from being unexpectedly broken by the penetrating member to leak a liquid for analysis.

As the first moving mechanism and second moving mechanism, preferably, the first moving mechanism includes a holding body that holds the penetrating member, and a guiding part that is provided in the container holder part and guides the holding body such that the penetrating member is positioned at the hole making position or the receding position; and the second moving mechanism includes a flexure part or a hinge part that is, in the holding body, provided between a guided part guided by the guiding part and the penetrating member. If so, the second moving mechanism is provided in the holding body, and therefore a configuration of the body fluid analysis fixture can be simplified. In particular, in the case where the second moving mechanism is configured to have the flexure part, it is only necessary to provide a structure or material having flexibility between the guided part and a holding part in the holding body, and therefore the configuration can be further simplified.

In order to, in a state where the penetrating member is at the receding position, prevent the sealing film from being broken by external contact other than the contact by the penetrating member, preferably, the holding body has, at the receding position, a cover part that is positioned on the upper side in the out-of-plane direction of the sealing member and protects the sealing member from outside.

In order to, along with the movement of the penetrating member by the first moving mechanism, enable a body fluid to be quantitatively collected and also simplify the configuration of the body fluid analysis fixture, preferably, the guiding part has: an upstream side capillary flow path that is formed in series with a body fluid inlet; and a downstream side capillary flow path that is formed by sandwiching a space with the upstream side capillary flow path; the holding body has a quantity determining capillary flow path that is slidably provided in the space; communicatively connects the upstream side capillary flow path and the downstream side capillary flow path; and quantifies a body fluid introduced from the body fluid inlet; at the receding position, the upstream side capillary flow path, the quantity determining capillary flow path, and the downstream side capillary flow path are communicatively connected; and at the hole making position, the quantity determining capillary flow path is communicatively connected to a flow path through which the liquid for analysis flows.

Advantageous Effects of Invention

According to the present invention configured as described, in a configuration in which a liquid container for analysis sealed by a sealing member is penetrated by a penetrating member, the sealing film can be prevented from being unexpectedly broken by the penetrating member to leak a liquid for analysis.

DETAILED DESCRIPTION OF THE EMBODIMENTS

One embodiment of a body fluid analyzer using a body fluid analysis fixture according to the present invention will hereinafter be described with reference to the drawings.

Figure 1:
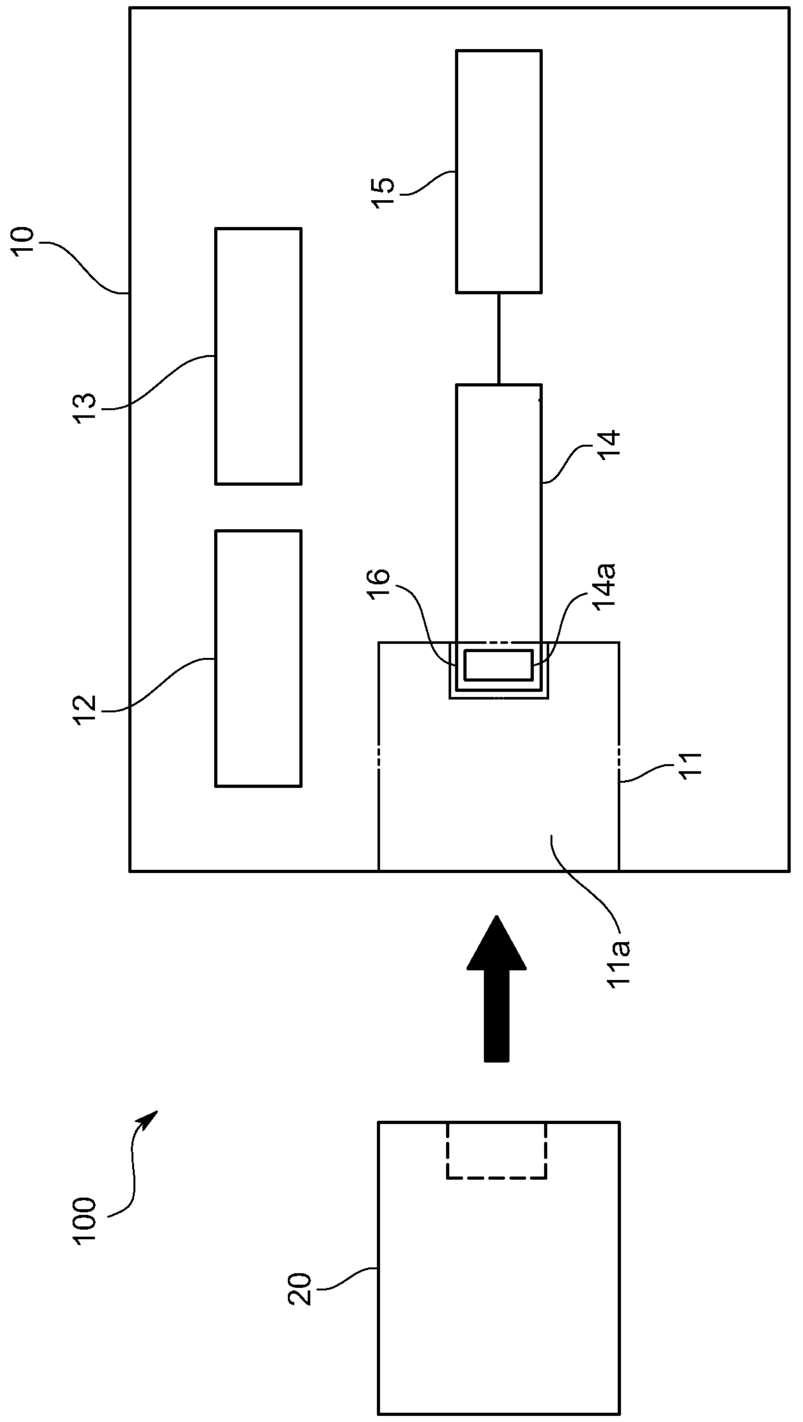
FIG. 1 is an overall schematic diagram schematically illustrating a configuration of a body fluid analyzer according to the present embodiment.

A body fluid analyzer 100 according to the present embodiment is, as illustrated in FIG. 1, provided with a measuring part main body 10, and a cartridge 20 that is detachably attached to the measuring part main body 10 and serves as a body fluid analysis fixture. The measuring part main body 10 is provided with: an attachment part 11 that is to be attached with the cartridge 20; a drive part 12 that drives a slide body 202 (to be described later) provided in the cartridge 20 to make a slide movement or the like; a liquid supply part 13 that is intended to circulate diluted specimen blood (hereinafter simply referred to as diluted blood), which serves as a liquid to be measured, inside the cartridge 20; a connector part 14 that is intended to extract a signal from the cartridge 20; and a calculation part 15 that detects the electrical signal from the connector part 14 to calculate blood cells contained in the diluted blood.

The attachment part 11 is formed to be slightly larger than a width and a thickness of a fore end that is an insertion side end part of the cartridge 20, and provided with a groove-like concave part 11*a* (see FIG. 1) that is configured to have a predetermined depth in conformity to a shape of the insertion side end part of the cartridge 20. When the cartridge 20 is inserted into the concave part 11*a*, one part (including a blood quantity determination part 22) for gripping the cartridge 20 is positioned outside the attachment part 11. Also, a deep part of the concave part 11*a* is formed with a projection part 16 that fits into a cutout part 21 (see FIGS. 2 and 3, and other diagrams) formed in the fore end of the cartridge 20, and on a surface of the projection part 16, a part (conduction part 14*a*) of the connector part 14 that comes into contact with electrodes 27, 28, and 221 provided in the cartridge 20 to receive the electrical signal is formed.

The drive part 12 is configured to use: an engaging pawl that is to engage with a locking part 202*a* (specifically, a locking hole, see FIG. 3 and other diagrams) provided in the slide body 202 of the cartridge 20; and a slide driving mechanism (not illustrated) that moves the engaging pawl in a slide direction and uses, for example, a rack-and-pinion mechanism, motor, and the like that. Also, the drive part 12 is one that, in order to quantify blood, slides the slide body 202 between a blood quantity determination position X (see FIG. 5) and a blood introduction position Y (see FIG. 6) for mixing quantified blood with a regent to introduce them into a mixing flow path 24 and a measuring flow path 25. In addition, as will be described later, the drive part 12 is also one that moves a penetrating needle 71 provided on the slide body 202 to a reagent container 3 side.

The liquid supply part 13 is configured to have a suction pump and a valve as main components. The suction pump is one that is, when the cartridge 20 is attached to the attachment part 11, connected to an end point opening part H of the measuring flow path 25 to be described later; depressurizes the opening part H; and sucks and introduces the quantified blood and reagent into the mixing flow path 24 and the measuring flow path 25.

The connector part 14 is provided with the conduction part 14*a* that is electrically conducted to an inside of the concave part 11*a* of the attachment part 11, and one that, when the cartridge is attached, comes into contact with the electrodes 28 of the cartridge 20 to apply a predetermined voltage between the electrodes 28, and detects, as the electrical signal, a current amount proportional to an electrical resistance generated at the time of the application. Then, the connector part 14 outputs the electrical signal to the calculation part 15 through a wiring line such as a lead.

The calculation part 15 is provided with an electrical circuit (not illustrated) that converts the electrical signal outputted from the connector part 14 to a pulse signal to output it as a blood cell count and a blood cell volume value in the diluted blood introduced into the measuring flow path 25. Then, the signal regarding the blood cell count and the blood cell volume outputted as described above is outputted to a display or the like.

Next, a detailed configuration of the cartridge 20 is described with reference to FIGS. 2 to 10.

Figure 2:
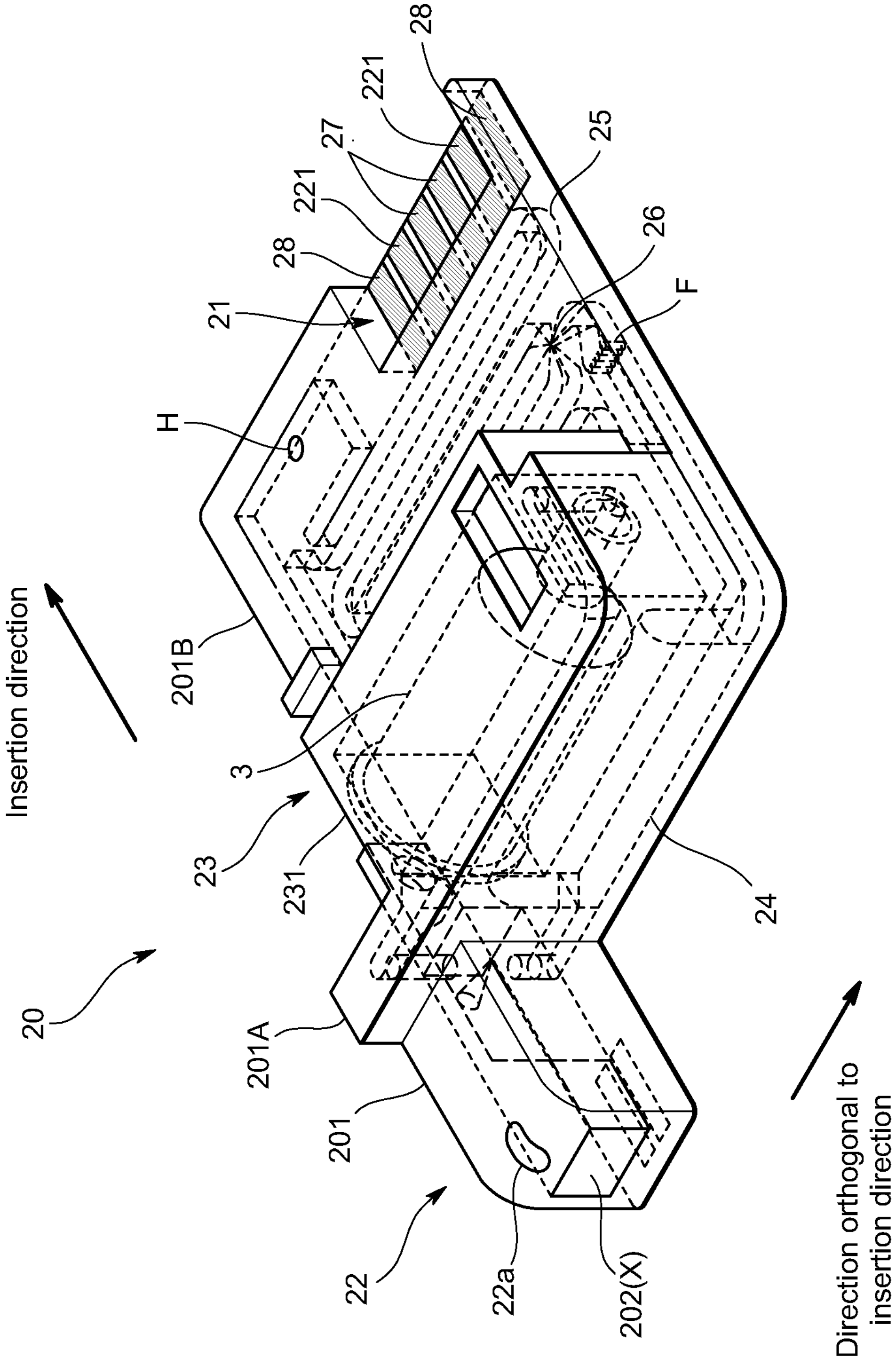
FIG. 2 is a perspective view of a cartridge in the same embodiment.
Figure 3:
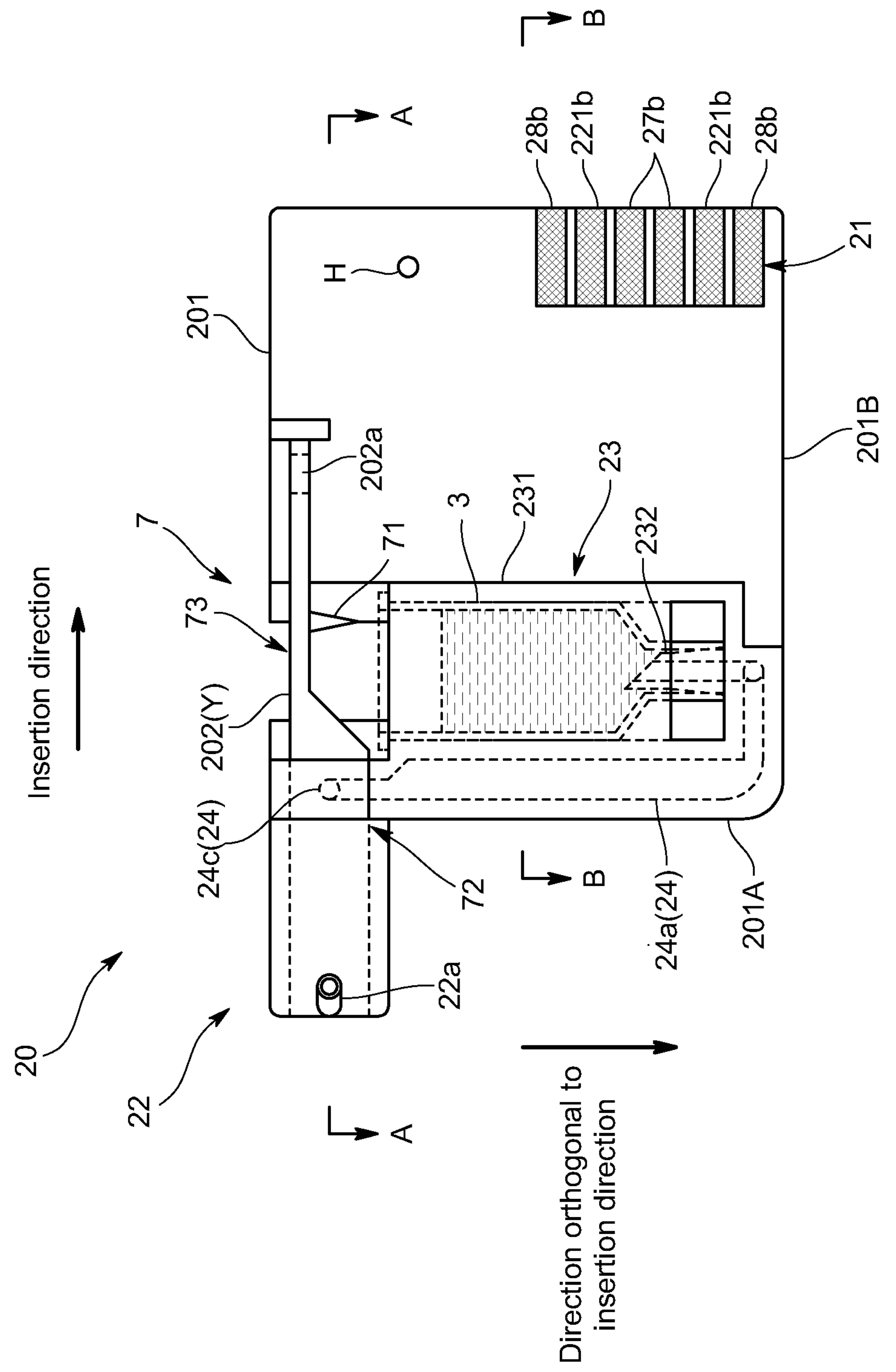
FIG. 3 is a front view illustrating flow paths and the like formed on a front surface side of the cartridge in the same embodiment.

As illustrated in FIGS. 2 and 3, the cartridge 20 is essentially a one-time disposable one, and provided with: the cutout part 21 having substantially a rectangular cross-sectional shape on the fore end side in an insertion direction thereof; and also near substantially the center of an end part on a side opposite to the fore end side in the insertion direction, the blood quantity determination part 22 having a blood inlet 22*a* that is opened on a surface of the blood quantity determination part 22. Also, the cartridge 20 is provided with: a container holder part 23 that is attached with a reagent container 3 for diluting blood quantified by the blood quantity determination part 22; the mixing flow path 24 for mixing the quantified blood and the reagent from the reagent container 3 with each other to stir them; and the measuring flow path 25 for measuring the blood cell count contained in the diluted blood that is formed by the mixing through the mixing flow path 24.

Figure 5:
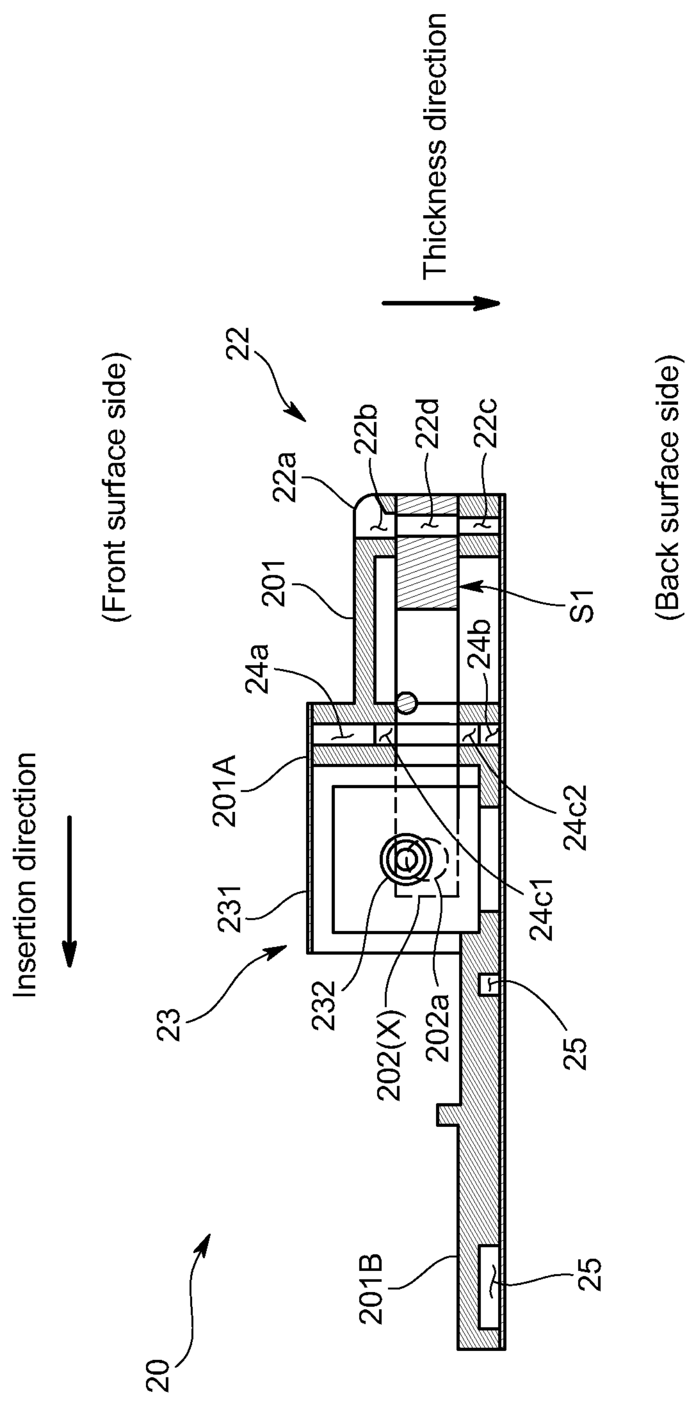
FIG. 5 is a cross-sectional view of the cartridge at a blood quantity determination position, taken along a line A-A of FIG. 3.
Figure 6:
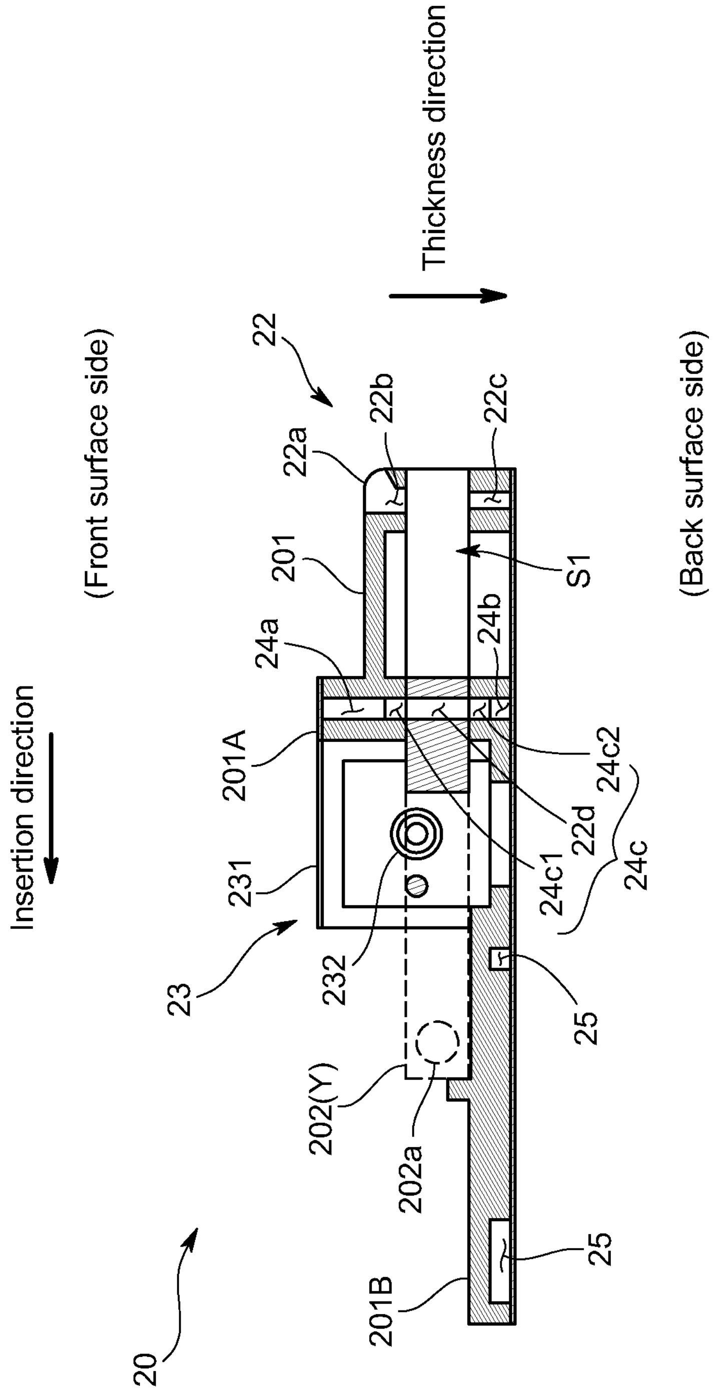
FIG. 6 is a cross-sectional view of the cartridge at a blood introduction position, taken along a line A-A of FIG. 3.

As illustrated in FIGS. 5 and 6, the blood quantity determination part 22 includes: a cartridge main body 201 having an upstream side capillary flow path 22*b* that is formed in series with the blood inlet 22*a* and is substantially linear, and a downstream side capillary flow path 22*c* that is formed by sandwiching a space S1 (space forming a slide path for the after-mentioned slide body 202) with the upstream side capillary flow path 22*b*, and is substantially linear; and the slide body 202 that is slidably provided in the space S1, communicatively connects the upstream side capillary flow path 22*b* and the downstream side capillary flow path 22*c* to each other, and is formed with a quantity determining capillary flow path 22*d* that quantifies blood introduced from the blood inlet 22*a* and has a predetermined flow path volume.

In this configuration, the engaging pawl of the drive part 12 engages with the locking part 202*a* formed in a fore end on the insertion direction side, and by the drive part 12, the slide body 202 slides between the blood quantity determination position X (FIG. 5) where the quantity determining capillary flow path 22*d* is communicatively connected to the upstream side capillary flow path 22*b* and the downstream side capillary flow path 22*c* and the blood introduction position Y (FIG. 6) where the quantity determining capillary flow path 22*d* is communicatively connected to an after-mentioned front surface side connecting flow path part 24*c*1 and the back surface side connecting flow path part 24*c*2. In addition, in a state where the quantity determining capillary flow path 22*d*, the front surface side flow path part 24*c*1, and the back surface side connecting flow path part 24*c*2 are communicatively connected, they form a connecting flow path part 24*c* that makes a connection between a front surface side flow path part 24*a* and a back surface side flow path part 24*b* (see FIG. 6).

Figure 4:
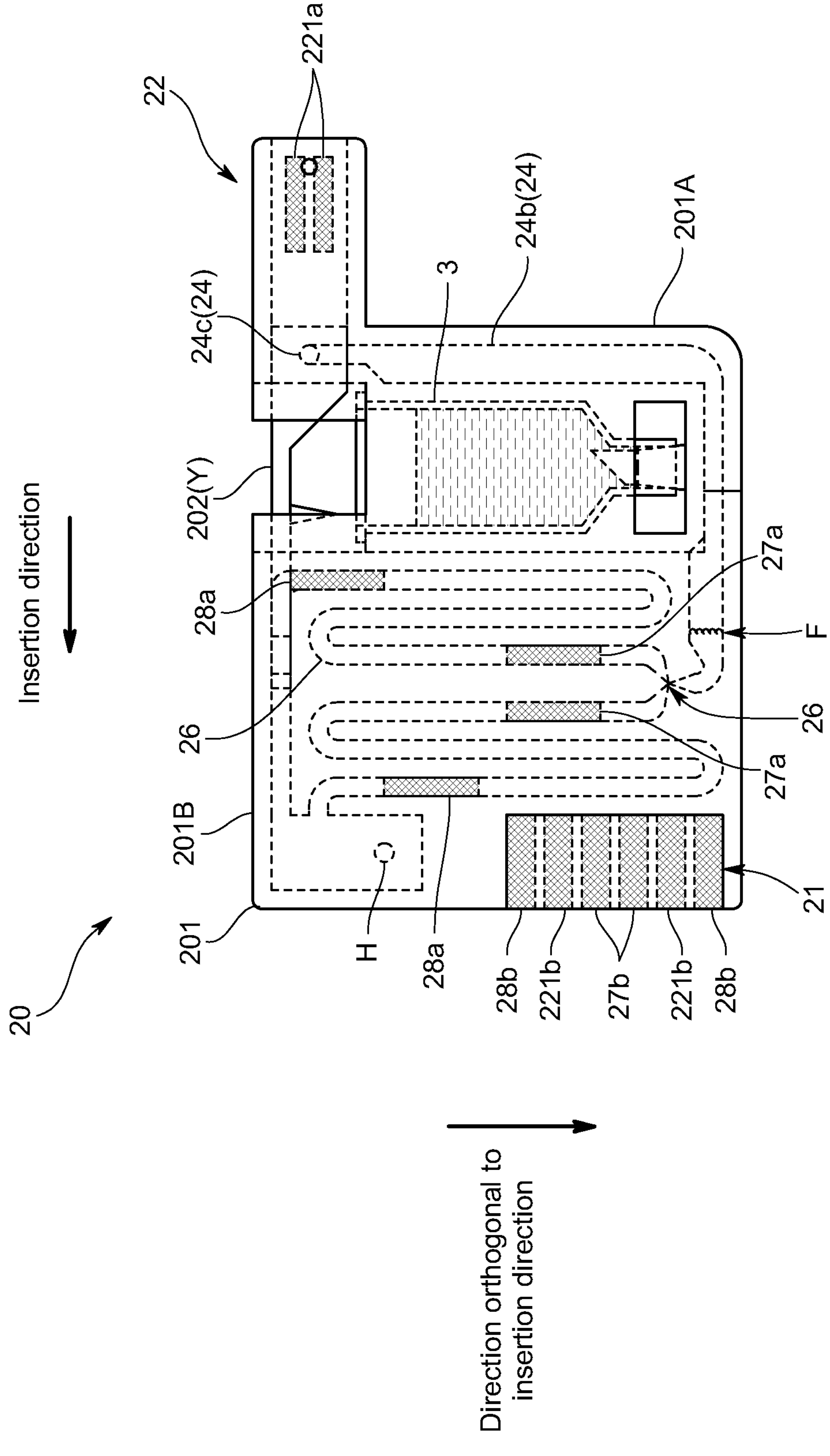
FIG. 4 is a back view illustrating flow paths and the like formed on a back surface side of the cartridge in the same embodiment.

Note that, in order to detect that the quantity determining capillary flow path 22*d* is filled with blood, as illustrated in FIG. 4, on a downstream side of the downstream side capillary flow path 22*c*, a liquid sensor 221 for detecting whether or not blood has reached is provided. The liquid sensor 221 is configured to have electrodes, and includes: a liquid contact part 221*a* that is provided so as to block all or part of a downstream side opening of the downstream side capillary flow path 22*c*; a lead (not illustrated) that is drawn from the liquid contact part 221*a*; and a signal extraction part 221*b* that is exposed on a cartridge surface below the cutout part 21 so as to be electrically conducted to the liquid contact part 221*a* through the lead.

Figure 7:
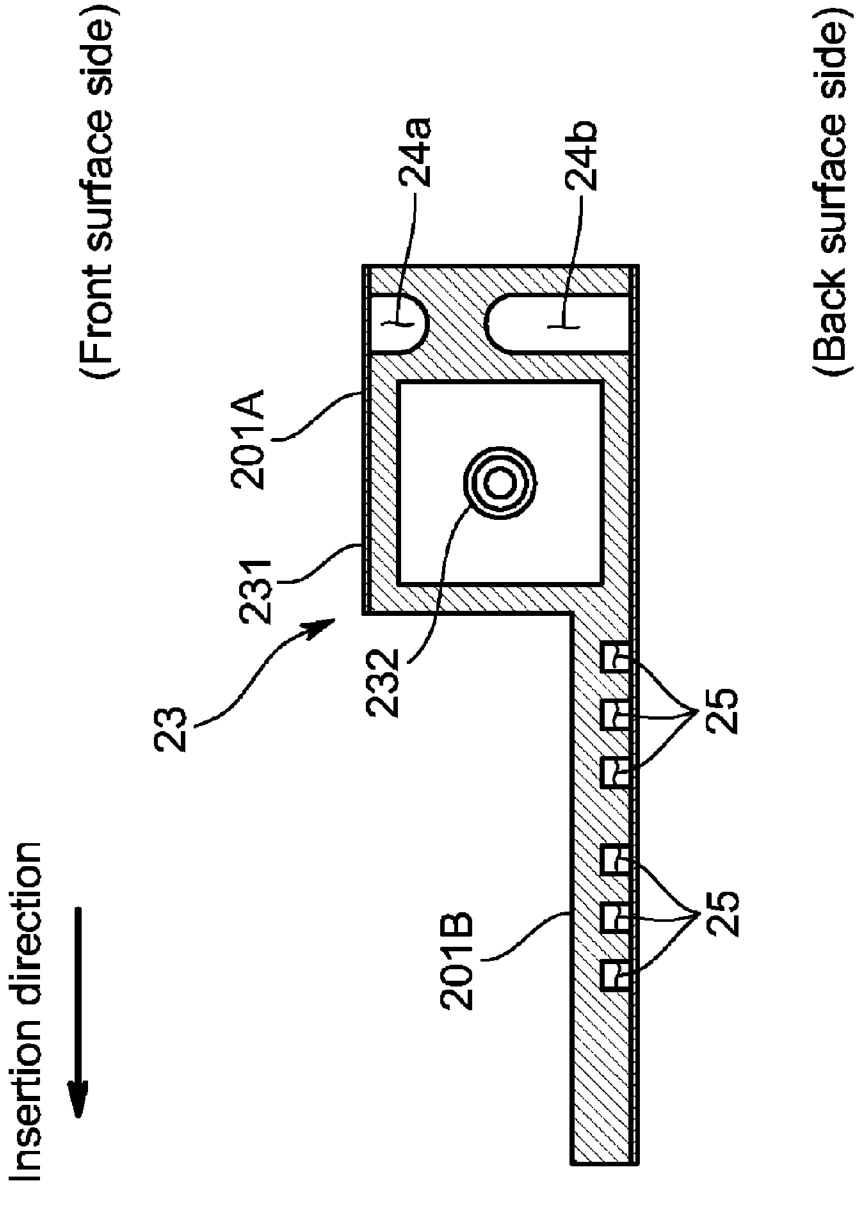
FIG. 7 is a cross-sectional view of the cartridge in the same embodiment, taken along a line B-B of FIG. 3.

The container holder part 23 is one that is detachably attached with the reagent container 3 serving as a liquid container for analysis, and specifically, as illustrated in FIGS. 5, 6 and 7, provided with: a container storage part 231 that is provided in a thick part 201A of the cartridge main body 201 and inserted with the reagent container 3 horizontally (in a direction orthogonal to the insertion direction) to store it; and a reagent lead-out needle 232 that is provided so as to extend from a bottom wall of the container storage part 231 and penetrates a seal part 32 of the reagent container 3 stored in the container storage part 231. The reagent lead-out needle 232 is communicatively connected to the mixing flow path 24 (front surface side flow path part 24*a*) of which an internal flow path is formed on a front surface side (i.e., on a front surface side of the thick part 201A of the cartridge main body 201) of the container storage part 231.

Figure 8:
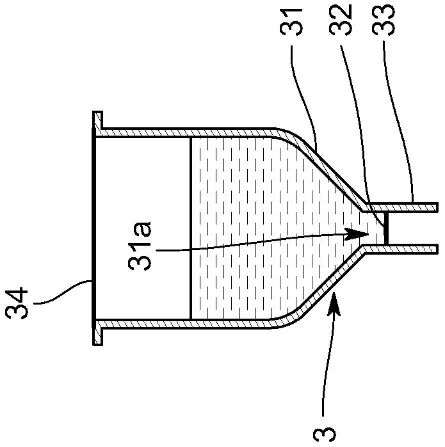
FIG. 8 is a cross-sectional view illustrating a configuration of a reagent container in the same embodiment.

Note that the reagent container 3 is one that contains the reagent serving as a predetermined quantity of liquid for analysis, and as illustrated in FIG. 8, provided with: a container main body 31 of which a bottom wall is formed with an opening part 31*a* that enables the reagent to be led out; the seal part 32 that seals the opening part 31*a*; and a guiding part 33 that is provided outside the seal part 32 and substantially cylindrically shaped.

The container main body 31 is substantially shaped as a body of revolution, has an axial dimension larger than a radial dimension, and has the bottom wall that is funnel shaped. Also, the opening part 31*a* is formed in substantially the center of the bottom wall. Further, the guiding part 33 is provided so as to cover a circumference of the seal part 32, and one that serves as a guide for inserting the reagent lead-out needle 232 into the seal part 32 and when the reagent lead-out needle 232 is inserted into the seal part 32, substantially liquid-tightly comes into contact with an outer circumferential surface of the reagent lead-out needle 232. The reagent container 3 of the present embodiment is made of resin such as polypropylene, and the container main body 31, the seal part 32, and the guiding part 33 are formed by integral molding. An upper part of the reagent container 3 is opened, and after the reagent has been contained from the opening, sealed by a sealing film 34 serving as a sealing member, such as an aluminum film. The reagent container 3 configured as described is stored in the container storage part 231 with an axial direction thereof being along the direction orthogonal to the insertion direction in a planar direction.

The mixing flow path 24 is formed on front and back surface sides of the thick part 201A of the cartridge main body 201, and one that mixes the blood quantified by the quantity determining capillary flow path 22*d* of the slide body 202 and the reagent from the reagent container 3 with each other to stir them. Specifically, as illustrated in FIGS. 3 to 7, the mixing flow path 24 includes: the front surface side flow path part 24*a* that is formed on a side wall front surface side of the container storage part 231 of the container holder part 23; the back surface side flow path part 24*b* that is formed on a side wall back surface side of the container storage part 231; and the connecting flow path part 24*c* that is formed in a side wall thickness direction of the container storage part 231 and connects the front surface side flow path part 24*a* and the back surface side flow path part 24*b* to each other.

The front surface side flow path part 24*a* is, as illustrated in, in particular, FIG. 3, formed on the side wall front surface side of the container storage part 231 in the direction orthogonal to the insertion direction in the planar direction. Also, the front surface side flow path part 24*a* has: an upstream side opening that is communicatively connected to an internal flow path of the reagent lead-out needle 232; and a downstream side opening that is communicatively connected to an upstream side opening of the connecting flow path part 24*c*.

The back surface side flow path part 24*b* is, as illustrated in, in particular, FIG. 4, similarly to the front surface side flow path part 24*a*, formed on the side wall back surface side of the container storage part 231 in the direction orthogonal to the insertion direction in the planar direction. Also, the back surface side flow path part 24*b* has: an upstream side opening that is communicatively connected to a down stream side opening of the connecting flow path part 24*c*; and a downstream side opening that is communicatively connected to an upstream side opening of the measuring flow path 25. Further, the downstream side opening of the front surface side flow path part 24*a* and the upstream side opening of the back surface side flow path part 24*b* configured as described are formed so as to substantially overlap with each other in a plan view.

The connecting flow path part 24*c* has, as illustrated in FIGS. 5 and 6 and other diagrams, the upstream side opening that is communicatively connected to the downstream side opening of the front surface side flow path part 24*a*, and the downstream side opening that is communicatively connected to the upstream side opening of the back surface side flow path part 24*b*, and is one that connects the front surface side flow path part 24*a* and the back surface side flow path part 24*b* to each other in a thickness direction.

Specifically, the connecting flow path part 24*c* is configured to have: the front surface side connecting flow path part 24*c*1 that is communicatively connected to the downstream side opening of the front surface side flow path part 24*a*; the back surface side connecting flow path part 24*c*2 that is formed by sandwiching the space S1 (space forming the slide path for the slide body 202) with the front surface side connecting flow path part 24*c*1, and communicatively connected to the upstream side opening of the back surface side flow path part 24*b*; and the quantity determining capillary flow path 22*d* of the slide body 202 that is slidably provided in the space S1. The front surface side connecting flow path part 24*c*1 has: one end that is communicatively connected to the front surface side flow path part 24*a*; and the other end that is opened to the space S1. Also, the back surface side connecting flow path part 24*c*2 has: one end that is opened to the space S1; and the other end that is communicatively connected to the back surface side flow path part 24*b*.

That is, when the slide body 202 is at the blood quantity determination position X, the connecting flow path part 24*c* is not formed, and therefore the front surface side flow path part 24*a* and the back surface side flow path part 24*b* are not communicatively connected to each other (see FIG. 5), whereas when the slide body 202 is at the blood introduction position Y, the connecting flow path part 24*c* is formed, and the front surface side flow path part 24*a* and the back surface side flow path part 24*b* are communicatively connected to each other (see FIG. 6). As described, when the slide body 202 is at the blood introduction position Y, the connecting flow path part 24*c* is formed, and also the quantified blood is introduced into the mixing flow path 24. In this state, the suction by the liquid supply part 13 causes the reagent to be introduced from the internal flow path of the reagent lead-out needle 232 inserted into the reagent container 3 into the front surface side flow path part 24*a*, the connecting flow path part 24*c*, and the back surface side flow path part 24*b*. Then, by the suction/discharge operation of the pump of the liquid supply part 13, the quantified blood and reagent are mixed in the mixing flow path 24 to form diluted blood.

As described, by configuring the mixing flow path 24 to have the front surface side flow path part 24*a*, the back surface side flow path part 24*b*, and the connecting flow path part 24*c*, the mixing flow path 24 can be formed in the thickness direction of the cartridge main body 201, and even though a volume of the mixing flow path 24 is made as large as possible, a plane size of the cartridge 20 is made compact. In particular, in the present embodiment, on a side wall of the container holder part 23 corresponding to the thick part 201A of the cartridge main body 201, the front surface side flow path part 24*a* and the back surface side flow path part 24*b* are formed in the thickness direction of the side wall, and therefore the volume of the mixing flow path 24 can be made as large as possible.

The measuring flow path 25 is, as illustrated in FIGS. 4 to 7, formed on a back surface side of a plate-like thin part 201B that serves as a measuring flow path forming part consecutively provided on a side surface on the insertion side of the thick part 201A of the cartridge main body 201. The plate-like thin part 201B is formed such that a back surface thereof coincides in height with a back surface of the thick part 201A of the cartridge main body 201. Also, the measuring flow path 25 is, as illustrated in FIG. 4, formed so as to be communicatively connected to a downstream side outlet of the mixing flow path 24 (specifically, the back surface side flow path part 24*b* of the mixing flow path 24), and from the downstream side outlet toward the insertion direction, formed all around on the back surface side of the plate-like thin part 201B of the cartridge main body 201. The measuring flow path 25 is narrowed on the upstream side thereof such that inner walls facing each other in the flow path 25 form a gap of approximately 1 mm, and by the gap, an aperture part 26 is formed. Note that a size of the gap for forming the aperture part 26 can be appropriately set depending on a size of a cell to be measured (in the present embodiment, a blood cell).

Figure 9:
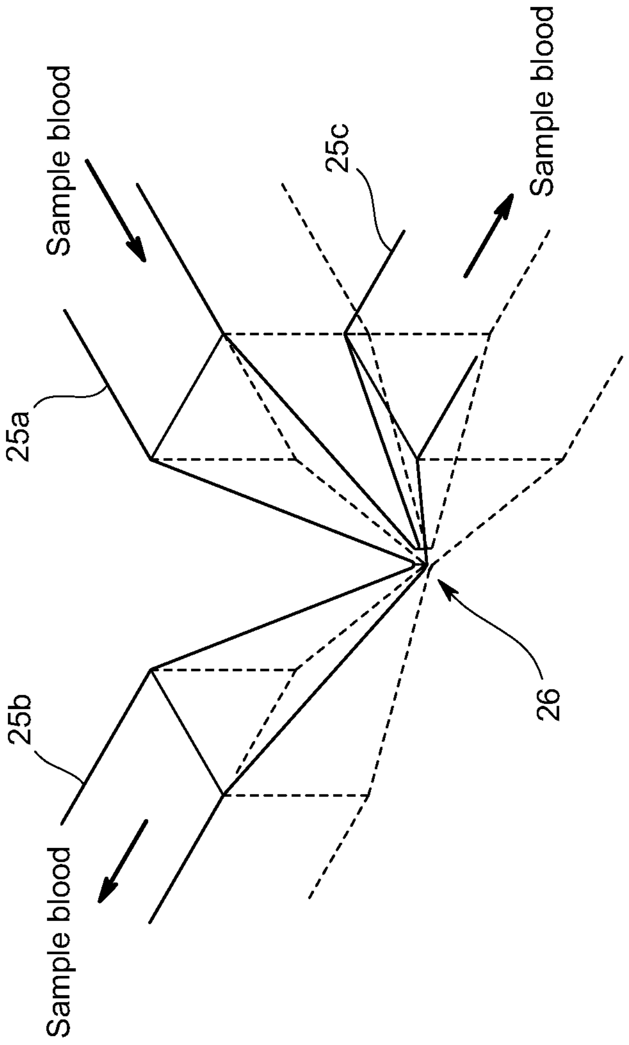
FIG. 9 is an enlarged perspective view illustrating an aperture part in the same embodiment.

Also, the measuring flow path 25 is, as illustrated in, in particular, FIG. 9, divided into two branches toward the downstream side from a position where the aperture part 26 is formed. In the measuring flow path 25 near the aperture part 26, the flow path 25*a* on the upstream side of the aperture part 26 is configured so as to gradually narrow a distance between the inner walls facing each other toward the aperture part 26, and each of the flow paths 25*b* and 25*c* on the downstream side is configured so as to gradually expand a distance between inner walls facing each other from the aperture part 26. In the other sites, a flow path width is almost constant. By forming the measuring flow path 25 as described, a flow of the diluted blood passing through the aperture part 26 is not disturbed, and blood cells contained in the diluted blood pass through the aperture part 26 in sequence.

Note that, on the upstream side of the aperture part 26, a filter part F for removing foreign substances such as dust and dirt each having a predetermined size (e.g., 50 μm or more) contained in the diluted blood is formed. The filter part F is formed of a plurality of columnar parts that are mutually arranged at predetermined intervals. This prevents the foreign substances from reaching the electrodes 27 and 28, and therefore measurement accuracy of the blood analysis can be improved.

To describe the flow paths 25*b* and 25*c* on the downstream side of the aperture part 26, each of the flow paths 25*b* and 25*c* is formed in a meandering shape that includes: a linear flow path that is formed from the branch position so as to pass across the insertion direction of the cartridge main body 201; and a bent flow path that bends the linear flow path (see FIG. 4). As described, the measuring flow path 25 is configured to bend multiple times on end part sides with respect to the insertion direction of the cartridge main body 201, and formed over substantially the entire area of the cartridge main body 201. This allows the measuring flow path 25 to be ensured as long as possible within a limited area inside the cartridge main body 201. Also, the measuring flow path 25 is configured such that a final end part thereof is communicatively connected to the opening part H opened on a surface (lower surface) of the cartridge main body 201, and the diluted blood introduced from a downstream side outlet (opening) of the mixing flow path 24 travels in the measuring flow path 25 so as to push out air contained in the measuring flow path 25 from the opening part H.

Also, as illustrated in FIG. 4, in positions that are on the downstream side of the aperture part 26 at the branch position of the measuring flow path 25, and in contact with the diluted blood having passed through the aperture part 26, the pair of electrodes 27 (hereinafter also referred to as first electrodes 27) serving as detection parts are arranged so as to sandwich the aperture part 26. In addition, each of the electrodes 27 includes: a liquid contact part 27*a* that is formed so as to face to the inner wall of the measuring flow path 25; a lead (not illustrated) that is drawn from the liquid contact part 27*a*; and a signal extraction part 27*b* that is exposed on the cartridge surface on the cutout part 21 so as to be electrically conducted to the liquid contact part 27*a* through the lead.

Further, on a downstream side of the liquid contact part 27*a* in the first electrode 27, the second electrode 28 is provided. The second electrode 28 is configured to have: a liquid detection part 28*a* that is provided on a downstream side where a flow path volume from the liquid contact part 27*a* becomes equal to a predetermined constant volume (specifically, on an upstream side from the end point of the measuring flow path 25 by a predetermined distance); a lead (not illustrated) that is drawn from the liquid detection part 28*a*; and a detected signal output part 28*b* that is in series with an end point of the lead and provided laterally to the signal extraction part 27*b*, and acts as a liquid level sensor adapted to detect that the diluted blood has reached the liquid detection part 28*a*.

That is, when the diluted blood traveling in the measuring flow path 25 after coming into contact with the liquid contact part 27*a* comes into contact with the liquid detection part 28*a*, an electrical signal is generated, and the electrical signal is sent to the detected signal output part 28*b* through the lead drawn from the liquid detection part 28*a*, which informs the measuring part main body 10 that the diluted blood has reached the predetermined reaching position in the measuring flow path 25. As described, when it is detected that the diluted blood has reached the predetermined position in the measuring flow path 25, the liquid supply part 13 stops supplying the diluted blood, and thereby the diluted blood can be prevented from reaching the opening part H at the end point of the flow path to overflow.

Note that the signal extraction part 27*b* of the first electrode 27 and the detected signal output part 28*b* of the second electrode 28 are, as described above, arranged side by side, and configured to, when the cartridge 20 is attached to the measuring part main body 10, come into electrical contact with the conduction part 14*a* of the connector part 14.

Also, the cartridge 20 of the present embodiment is, as illustrated in FIG. 3, provided with an atmospheric opening mechanism 7 that penetrates the sealing film 34 of the reagent container 3 stored in the container holder part 23 to open the reagent container 3 to the atmosphere.

The atmospheric opening mechanism 7 has: the penetrating needle 71 serving as a penetrating member that penetrates the sealing film 34 of the reagent container 3 held by the container holder part 23; a first moving mechanism 72 that moves the penetrating needle 71 in a direction orthogonal to an out-of-plane direction of the sealing film 34; and a second moving mechanism 73 that moves the penetrating needle 71 in the out-of-plane direction of the sealing film 34.

Figure 10:
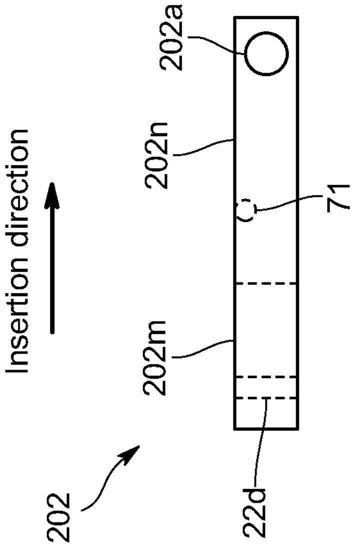
FIGS. 10 (*a-b*)is a diagram illustrating an atmospheric opening mechanism of the cartridge in the same embodiment.
Figure 10:
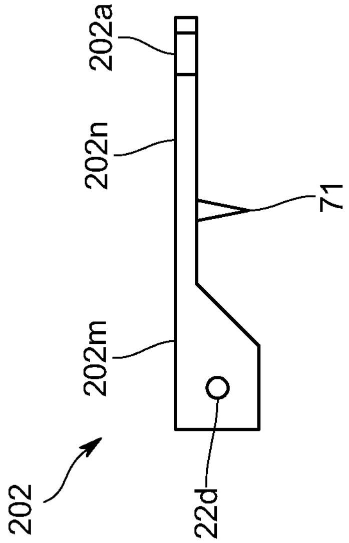

The penetrating needle 71 is provided so as to, on the insertion direction fore end side of the slide body 202 serving as a holding body, face to the reagent container 3 side. The slide body 202 is, as illustrated in FIG. 10, configured to have: a guided part 202*m* that slides while being in contact with side wall inner surfaces of the cartridge main body 201, which form the space S1 (slide path); and an extended part 202*n* that is provided so as to extend from the guided part 202*m* in the insertion direction, and thinner than the guided part 202*m*. On a reagent container 3 side of the extended part 202*n*, the penetrating needle 71 is provided, and on a fore end side further than the penetrating needle 71, the locking part 202*a* is formed.

Figure 11:
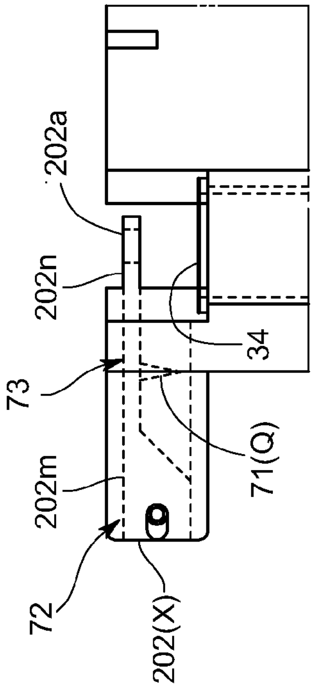
FIGS. 11 (*a-c*) is a diagram illustrating a slide body in the same embodiment.
Figure 11:
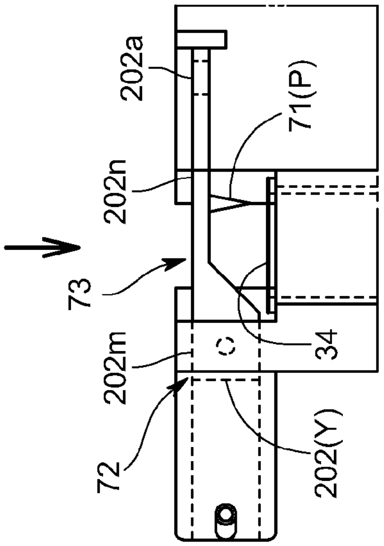
Figure 11:
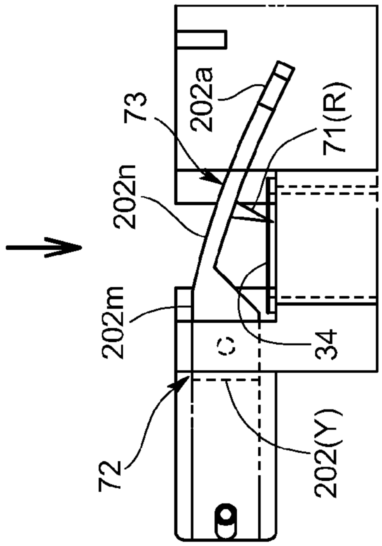

The first moving mechanism 72 is, as illustrated in FIG. 11, one that enables the penetrating needle 71 to be moved between a hole making position P that is an upper side in the out-of-plane direction of the sealing film 34 and a receding position Q that is separated from the hole making position P in the direction orthogonal to the out-of-plane direction of the sealing film 34 (i.e., the insertion direction, a plane direction of the sealing film 34). Note that the receding position Q is a position where the penetrating needle 71 is not present on the upper side in the out-of-plane direction of the sealing film 34, and in the present embodiment, corresponds to the blood quantity determination position X.

Specifically, the first moving mechanism 72 is configured to have the guided part 202*m* of the slide body 202 and the slide path serving as the guiding part provided in the cartridge main body 201. On the basis of the first moving mechanism 72, the slide body 202 moves back and forth along the insertion direction with respect to the reagent container 3. That is, the out-of-plane direction of the sealing film 34 of the reagent container 3 is a direction in which an outer surface of the sealing film 34 faces, and a direction orthogonal to the plane direction of the sealing film 34.

On the basis of the first moving mechanism 72 configured as described, the slide body 202 is driven by the above-described drive part 12. That is, the engaging pawl of the drive part 12 is made to engage with the locking part 202*a* of the slide body 202 to move the slide body 202 from the receding position Q to the hole making position P (see FIG. 11).

The slide body 202 is provided with the quantity determining capillary flow path 22*d* and the penetrating needle 71. Note that a position of the slide body 202 where the quantity determining capillary flow path 22*d* is at the blood quantity determination position X (the position where the upstream side capillary flow path 22*b*, the quantity determining capillary flow path 22*d*, and the downstream side capillary flow path 22*c* are communicatively connected), and a position of the slide body 202 where the penetrating needle 71 is at the receding position Q are the same. Also a position of the slide body 202 where the quantity determining capillary flow path 22*d* is at the blood introduction position Y (the position where the quantity determining capillary flow path 22*d* is communicatively connected to the measuring flow path 25), and a position of the slide body 202 where the penetrating needle 71 is at the hole making position P is the same. The slide body 202 enables blood to be quantified only by the movement of the slide body 202, and also the reagent container 3 to be opened to the atmosphere.

The second moving mechanism 73 is, as illustrated in FIG. 11, one that enables the penetrating needle 71 moved to the hole making position P by the first moving mechanism 72 to be moved toward the sealing film 34 to a penetrating position R where the penetrating needle 71 penetrates the sealing film 34. Note that the penetrating position R is a position where the penetrating needle 71 is inserted into the sealing film 34 to open the reagent container 3 to the atmosphere.

Specifically, the second moving mechanism 73 is configured to have a flexure part that is, in the slide body 202, provided between the guided part 202*m* and the penetrating needle 71. Note that the flexure part of the present embodiment uses flexure based on elastic deformation of the extended part 202*n*.

On the basis of the second moving mechanism 73 configured as described, the slide body 202 is driven by the above-described drive part 12. That is, by making the engaging pawl of the drive part 12 engage with the locking part 202*a* of the slide body 202 and moving the engaging pawl to the reagent container 3 side, the extended part 202*n* of the slide body 202 is pushed to the reagent container 3 side, and thereby the penetrating needle 71 is moved from the hole making position P to the penetrating position R (see FIG. 11).

Also, the slide body 202 has a cover part that is, at the receding position Q, positioned on the upper side in the out-of-plane direction of the sealing film 34 to protect the sealing film 34 from outside. In the present embodiment, the fore end side (part provided with the locking part 202*a*) further than the penetrating needle 71 in the extended part 202*n* functions as the cover part. This enables, in the state where the penetrating needle 71 is at the receding position Q, the sealing film 34 to be prevented from being broken by external contact other than the contact by the penetrating needle 71.

Figure 12:
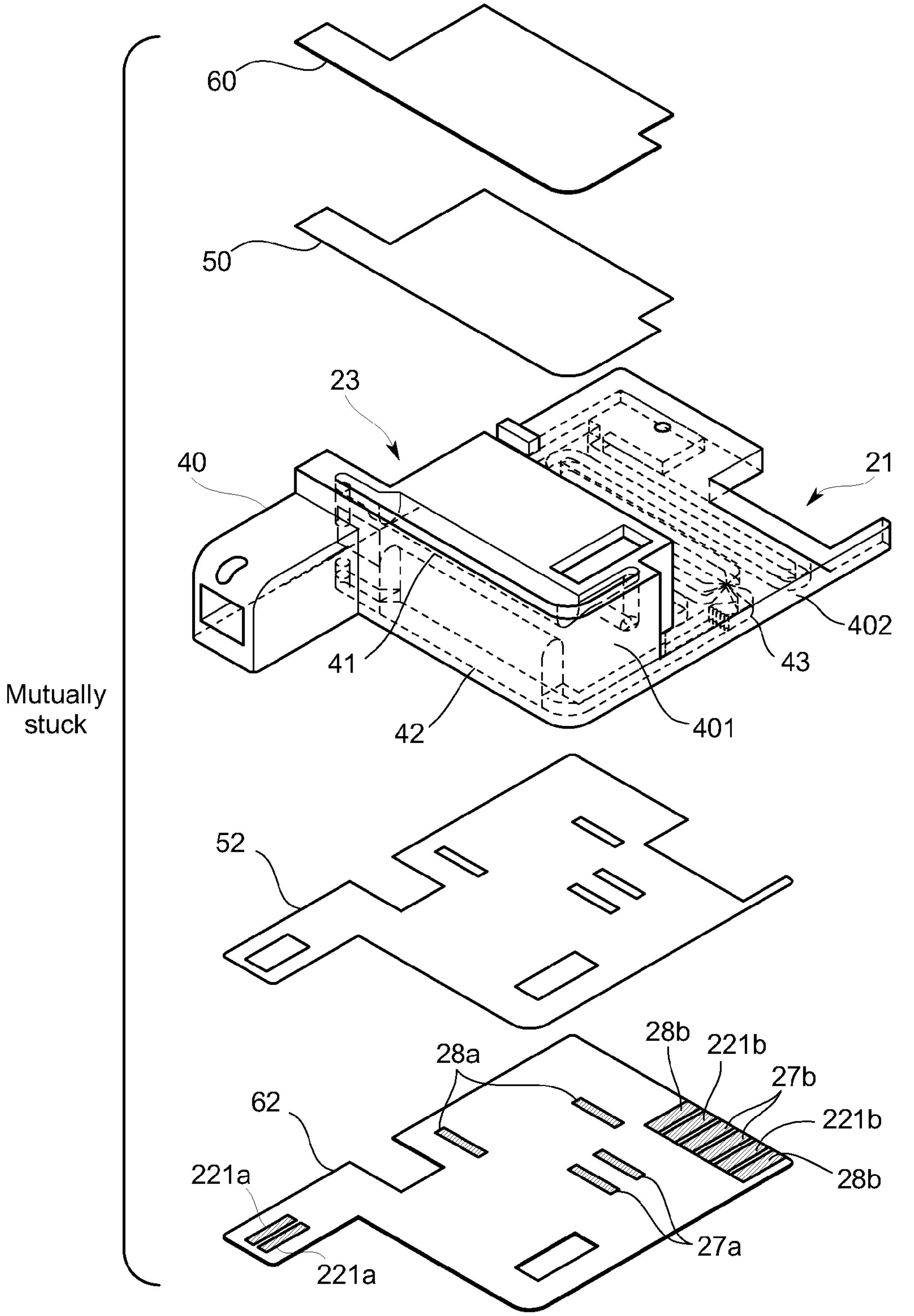
FIG. 12 is an exploded perspective view of a cartridge main body according to the same embodiment.

Next, details of an internal configuration of the cartridge main body 201 are described with reference to FIG. 12. The cartridge main body 201 is, as illustrated in FIG. 12, configured to have: a base material 40 made of, for example, PMMA, in which on front and back surfaces of a thick part 401, bottom-equipped grooves 41 and 42 are formed, and also on a back surface of a thin part 402, a bottom-equipped groove 43 is formed; and first and second films 60 and 62 that are stuck on front and back surfaces of the base material 40 through first and second adhesive sheets 50 and 52 and serve as cover members made of PET, respectively.

On the front surface of the thick part 401 of the base material 40, the first bottom-equipped groove 41 that forms the front surface side flow path part 24*a* of the mixing flow path 24 is formed, and on the back surface of the thick part 401, the second bottom-equipped groove 42 that forms the back surface side flow path part 24*b* of the mixing flow path 24 is formed. Also, at a downstream side end part of the first bottom-equipped groove 41, the front surface side connecting flow path part 24*c*1 of the connecting flow path part 24*c* is formed, and at an upstream side end part of the second bottom-equipped groove 42, the back surface side connecting flow path part 24*c*2 of the connecting flow path 24*c* is formed. Further, inside the thick part 401, the container holder part 23 is formed, and also a flow path that makes a connection between the internal flow path of the reagent lead-out needle 232 in the container holder part 23 and an upstream side end part of the first bottom-equipped groove 41 is formed. Still further, the slide body 202 is inserted into the space S1 formed inside the thick part 401.

Also, on the back surface of the thin part 402 of the base material 40, the third bottom-equipped groove 43 that forms the measuring flow path 25 is formed. A start point of the third bottom-equipped groove 43 is in series with an end point of the second bottom-equipped groove. Also, as described above, near the upstream side of the position where the aperture part 26 is formed, a width of the third bottom-equipped groove 43 is gradually narrowed, whereas near the downstream side of the position where the aperture part 26 is formed, the width of the third bottom-equipped groove 43 is gradually expanded. Such bottom-equipped grooves 41 to 43 and columnar parts of the filter part F are formed from the base material surfaces by any fabrication method such as micromachining fabrication, hot emboss fabrication, or optical molding.

Also, the first film 60 is formed to have a shape that substantially coincides with a surface shape of the thick part 401 of the base material 40, and when stuck on the thick part front surface of the base material 40, covers an opening part of the first bottom-equipped groove 41 to thereby form the front surface side flow path part 24*a* of the mixing flow path 24. Further, the second film 62 is formed to have a shape that substantially coincides with surface shapes of the thick part 401 and the thin part 402 of the base material 40, and when stuck on the back surface of the base material 40, covers opening parts of the second and third bottom-equipped grooves 42 and 43 to thereby form the back surface side flow path part 24*b* of the mixing flow path 24 and the measuring flow path 25. Also, the second film 62 is formed with a through-hole 62*a* at a position corresponding to an end point of the third bottom-equipped groove 43. Further, the second film 62 is not provided with a cutout in a position corresponding to the cutout part 21 of the base material 40, and configured such that when the base material 40 and the second film 62 are bonded to each other, a part of the film 62 covers an upper side of the cutout part 21. In addition, in the area covering the upper side of the cutout part 21, the signal extraction part 27*b* that is a part of the first electrode 27, the detected signal output part 28*b* that is a part of the second electrode 28, and the signal extraction part 221*b* that is a part of the liquid sensor 221 are formed.

Also, by applying a thin carbon coat (C) on a small amount of silver (Ag) that is coated in predetermined positions on a surface of the second film 62 and serves as conductive metal, the above-described first and second electrodes 27 and 28 are formed. As described above, the liquid contact part 27*a* and the liquid detection part 28*a* respectively constituting these electrodes come into contact with the diluted blood flowing through the measuring flow path 25 to be thereby electrically conducted to each other, and are further electrically connected to the signal extraction part 27*b* and the detected signal output part 28*b* through the leads, respectively. In addition, the liquid sensor 221 is formed in the same manner. Further, the first electrode and the like are formed by a method such as screen printing or sputtering.

Also, the first adhesive sheet 50 for bonding the front surface of the thick part of the base material 40 and the first film 60 to each other is formed of a thin film like solid adhesive 50 that covers the entire front surface of thick part of the base material 40. On the other hand, the second adhesive sheet 52 for bonding the back surface of the base material 40 and the second film 62 to each other is formed of a thin film like solid adhesive that covers the entire back surface of the base material 40 except for parts corresponding to the locations of the second film 62 where the liquid contact parts 27*a*, the liquid detection parts 28*a*, and the liquid contact parts 221*a* are formed. The solid adhesive is solid at room temperature; however, it has a character in which when it is heated to a predetermined temperature or more, it melts to give rise to adhesive property. By sandwiching the solid adhesives 50 and 52 between the base material 40 and the first and second films 60 and 62, and heating them in this state, the base material 40 and the first and second films 60 are bonded to each other.

<Measuring Procedure>

Next, a procedure to use such a body fluid analyzer 100 to measure a blood cell count and a blood cell size in the diluted blood is described below.

First, the reagent container 3 is stored in the container holder part 23 of the cartridge main body 201. At this time, the reagent lead-out needle 232 of the container holder part 23 is not yet inserted into the seal part 32. Also, a position of the slide body 202 with respect to the cartridge main body 201 corresponds to the blood quantity determination position X. In this state, the cartridge 20 is attached to the measuring part main body 10. Then, the reagent container 3 is attached to the container holder part 23, and the reagent lead-out needle 232 is inserted into the seal part 32. In addition, at this time, the signal extraction parts 27*b*, the detected signal output parts 28*b*, and signal extraction parts 221*b* formed on the surface of the cartridge main body 201 come into contact with the conduction part 14*a* of the connector part 14 to supply a small amount of current so as to apply a predetermined voltage from the conduction part 14*a* to the liquid sensor 221, and the first and second electrodes 27 and 28 of the cartridge main body 201.

Then, blood is attached to the blood inlet 22*a* of the cartridge main body 201, which is exposed outside the measuring part main body 10. By doing so, the attached blood is introduced inside on the basis of the capillary phenomenon by the upstream side capillary flow path 22*b*, the quantity determining capillary flow path 22*d*, and the downstream side capillary flow path 22*c*. At this time, the measuring part main body 10 obtains a detected signal from the liquid sensor 221 provided at the downstream side opening of the downstream side capillary flow path 22*c* to determine whether or not the blood has reached the downstream side capillary flow path 22*c*. If the measuring part main body 10 determines that the blood has reached the downstream side capillary flow path 22*c*, the measuring part main body 10 slides the slide body 202 from the blood quantity determination position X to the blood introduction position Y. At this time, blood outside the quantity determining capillary flow path 22*d* is struck by a forming wall part forming the upstream side capillary flow path 22*b* and a forming wall part forming the downstream side capillary flow path 22*c*, and only the blood retained in the quantity determining capillary flow path 22*d* moves to the blood introduction position Y.

Also, at this time, the measuring part main body 10 pushes the extended part 202*n* of the slide body 202 to the reagent container 3 side, and thereby penetrates the sealing film 34 of the reagent container 3 with the penetrating needle 71 to open the reagent container 3 to the atmosphere.

After the slide body 202 has been moved to the blood introduction position Y, the liquid supply part 13 operates to depressurize the mixing flow path 24, and thereby the reagent is sucked into the mixing flow path 24 from the reagent container 3. Then, the liquid supply part 13 performs the suction operation and discharge operation of the pump to thereby mix the blood and the reagent in the mixing flow path 24 and/or the reagent container 3. After the mixing, by the liquid supply part 13, the diluted blood is sucked into the measuring flow path 25.

When the diluted blood supplied into the measuring flow path 25 passes through the aperture part 26 and is branched, and the branched diluted blood flows respectively reach the pair of liquid contact parts 27*a*, the connector part 14 detects an electrical resistance value between the liquid contact parts 27*a* as an electrical signal through the signal extraction parts 27*b*. The electrical signal is a pulse signal proportional to the electrical resistance value that is varied on the basis of a blood cell count and volume (diameter) in the diluted blood passing through the aperture part 26, and the connector part 14 calculates, from the electrical signal, the blood cell count and volume in the diluted blood having passed through the aperture part 26 for a predetermined period of time (for example, a period of time from a time point when the diluted blood reaches the liquid contact parts 27*a* of the first electrodes 27 to a time point when it reaches the liquid detection parts 28 of the second electrodes 28), and then outputs a result of the calculation to the display, or the like.

Also, when the diluted blood supplied into the measuring flow path 25 passes through the positions where the first electrode liquid contact parts 27*a* are provided, and further reaches the positions where the second electrode liquid detection parts 28*a* are provided, an electrical resistance value between the second electrodes 28 is detected as an electrical signal through the detected signal output parts 28*b*. When the electrical signal is detected in the connector part 14, the calculation is stopped, and also a switching valve is operated to switch the opening part H from the liquid supply part 13 and communicatively connect the opening part H to the atmosphere. This returns the opening part H to the atmospheric pressure to stop the suction of the diluted blood.

When the measurement of the blood cell count in the diluted blood is completed as described, the cartridge 20 is detached from the attachment part 11, and the cartridge 20 in a state of containing the diluted blood is discarded according to a predetermined process such as incineration.

<Effects of the Present Embodiment>

According to the body fluid analyzer 100 configured as described according to the present embodiment, the penetrating operation on the sealing film 34 by the penetrating needle 71 can be performed so as to move from the receding position Q to the hole making position P along the direction orthogonal to the out-of-plane direction of the sealing film 34 and then moves to the penetrating position R. Based on this, because before the penetrating operation, the penetrating needle 71 is at the receding position Q, the penetrating needle 71 can be prevented from unexpectedly coming into contact with the sealing film 34 before the penetrating operation. Accordingly, the sealing film 34 can be prevented from being unexpectedly broken by the penetrating needle 71 to leak the reagent outside.

<Other Variations>

Note that the present invention is not limited to the above-described embodiment.

For example, the above-described embodiment is configured such that the connecting flow path part is configured to have the front surface side connecting flow path part, the quantity determining capillary flow path, and the back surface side connecting flow path part, and the connecting flow path part is used to introduce quantified blood into the mixing flow path; however, the present invention is not limited to this. That is, the present invention may be configured not to use the connecting flow path part to introduce the quantified blood, but to use the connecting flow path only for the connection between the front surface side flow path part and the back surface side flow path part.

Also, the mixing flow path of the above-described embodiment is formed only on the front and back surface sides of the container holder part; however, the mixing flow path may be formed over the entire area of the thin part of the cartridge main body. Specifically, the back surface side flow path part may be formed over the entire area of the thin part of the cartridge main body. On the other hand, the measuring flow path may be formed over the entire area of the thick part of the cartridge main body.

Further, the above-described embodiment is configured to form the mixing flow path on the front and back surface sides of the cartridge main body; however, the measuring flow path may be formed on the front and back surface sides of the cartridge main body.

Further, the second moving mechanism of the above-described embodiment is configured to have a flexure part using elastic deformation of the extended part; however, besides, the present invention may be configured to provide a hinge part between the guided part and the penetrating needle.

In addition, the penetrating member of the above-described embodiment is the penetrating needle having a needle shape that is tapered toward a fore end; however, besides, the penetrating member is only required to be one that penetrates the sealing member to open it to the atmosphere, and for example, may be a rod-like one having, for example, substantially a uniform cross-sectional shape. In this case, as a fore end shape, for example, it is possible to form a spherical shape or an angular shape.

Besides, it should be appreciated that the present invention is not limited to the above-described embodiment, and can be variously modified without departing from the scope thereof.

Reference Characters List

100: Body fluid analyzer
20: Cartridge (body fluid analysis fixture)
201: Cartridge main body (fixture main body)
202: Slide body (holding body)
202*m*: Guided part
22*a*: Body fluid inlet
22*b*: Upstream side capillary flow path
22*c*: Downstream side capillary flow path
22*d*: Quantity determining capillary flow path
23: Container holder part
3: Reagent container (liquid container for analysis)
34: Sealing film
71: Penetrating needle (penetrating member)
72: First moving mechanism
73: Second moving mechanism
F: Hole making position
Q: Receding position
R: Penetrating position

The invention claimed is:

1. A body fluid analysis fixture having:

a cartridge main body is provided with a container holder part that holds a liquid container for analysis that is sealed by a sealing member and is provided with a flow path through which a liquid for analysis flows;

a slide body is slidably provided in the cartridge main body and slides with respect to the container holder part; and wherein the slide body is provided with a penetrating member that is configured to selectively penetrate the sealing member of the liquid container for analysis held by the container holder part, and a quantity determining capillary flow path that has a predetermined flow path volume for quantifying blood that is alternately drawn in and released from the quantity determining capillary flow path;

wherein with sliding of the slide body, the penetrating member moves between a hole making position that is an upper side in an out-of-plane direction of the sealing member and a receding position that is separated from the hole making position in a direction orthogonal to the out-of-plane direction of the sealing member; and wherein the penetrating member moves to a penetrating position in order to penetrate the sealing member when the penetrating member is located in the hole making position; and wherein at the receding position the quantity determining capillary flow path is communicatively connected to a body fluid inlet to draw the blood into the quantity determining capillary flow path, and at the hole making position, the quantity determining capillary flow path is communicatively connected to the flow path through which the liquid for analysis flows for releasing the blood as the liquid for analysis to the flow path.

2. The body fluid analysis fixture according to claim 1, further comprising:

a guiding part that is provided in the container holder part and guides the slide body such that the penetrating member is positioned at the hole making position or the receding position to move the penetrating member between the hole making position and the receding position; and a flexure part or a hinge part that is, in the slide body, provided between a guided part guided by the guiding part and the penetrating member to move the penetrating member between the penetrating position and the hole making position.

3. The body fluid analysis fixture according to claim 2, wherein the slide body has, at the receding position, a cover part that is positioned on the upper side in the out-of-plane direction of the sealing member and protects the sealing member from outside.

4. The body fluid analysis fixture according to claim 2, wherein:

the guiding part has: an upstream side capillary flow path that is formed in series with the body fluid inlet; and a downstream side capillary flow path that is formed by sandwiching a space with the upstream side capillary flow path;

the slide body is slidably provided in the space and has a quantity determining capillary flow path that communicatively connects the upstream side capillary flow path and the downstream side capillary flow path; and quantifies a body fluid introduced from the body fluid inlet; and at the receding position, the upstream side capillary flow path, the quantity determining capillary flow path, and the downstream side capillary flow path are communicatively connected.

* * * * *